United States Patent
Toso

(10) Patent No.: US 9,943,619 B2
(45) Date of Patent: Apr. 17, 2018

(54) SANITIZING MACHINE

(71) Applicant: Mauro Toso, Rovigo (IT)

(72) Inventor: Mauro Toso, Rovigo (IT)

( * ) Notice: Subject to any disclaimer, the term of this patent is extended or adjusted under 35 U.S.C. 154(b) by 360 days.

(21) Appl. No.: 14/411,461

(22) PCT Filed: Jun. 25, 2013

(86) PCT No.: PCT/IB2013/001325
§ 371 (c)(1),
(2) Date: Dec. 26, 2014

(87) PCT Pub. No.: WO2014/001873
PCT Pub. Date: Jan. 3, 2014

(65) Prior Publication Data
US 2015/0335775 A1    Nov. 26, 2015

(30) Foreign Application Priority Data

Jun. 25, 2012    (IT) ............... RO2012A0003
Feb. 19, 2013    (IT) ............... RO2013A0003

(51) Int. Cl.
*A61L 2/18*      (2006.01)
*A61L 2/20*      (2006.01)
(Continued)

(52) U.S. Cl.
CPC .............. *A61L 2/18* (2013.01); *A45C 5/03* (2013.01); *A61L 2/202* (2013.01); *A61L 2/24* (2013.01); *B08B 9/0826* (2013.01); *B08B 9/0861* (2013.01); *A45C 5/00* (2013.01); *A45C 13/001* (2013.01); *A61L 2202/122* (2013.01)

(58) Field of Classification Search
CPC .................... A61L 2/18; A61L 2/202
See application file for complete search history.

(56) References Cited

U.S. PATENT DOCUMENTS 3,667,134 A * 6/1972 Rockson .............. A61L 9/20
                                                                    34/202
3,837,915 A    9/1974   Erb
(Continued)

FOREIGN PATENT DOCUMENTS

JP         2011067498 A     4/2011
KR        200441324 Y1     8/2008
(Continued)

OTHER PUBLICATIONS

English Abstract of RU2088221 dated Aug. 27, 1997.
International Search Report in corresponding PCT application dated Oct. 14, 2013.

*Primary Examiner* — Donald R Spamer
(74) *Attorney, Agent, or Firm* — Hedman & Costigan, P.C.; James V. Costigan; Kathleen A. Costigan

(57) ABSTRACT

A sanitizing machine comprising a supporting structure which includes two compartments or chambers (A, B), wherein, when the machine is in stand-by, a first compartment (A) is open and is able to house at least one container or object (V) to sanitize, while a second compartment (B) of the machine houses a sliding door (SP), which hermetically and automatically closes (D3) the first compartment (A) when the machine is on. The method thereof provides for at least one type of sanitizing cycle, such as a ozone cycle, a sanitizing liquid cycle and a combined cycle.

8 Claims, 2 Drawing Sheets

(51) Int. Cl.
*A61L 2/24* (2006.01)
*A45C 5/03* (2006.01)
*B08B 9/08* (2006.01)
*A45C 5/00* (2006.01)
*A45C 13/00* (2006.01)

(56) References Cited

U.S. PATENT DOCUMENTS

2003/0051300 A1* 3/2003 Ferrari .................... A47L 23/02
  15/36
2004/0003511 A1   1/2004 Silver
2005/0193585 A1*  9/2005 Silver ....................... F26B 9/06
  34/201

FOREIGN PATENT DOCUMENTS

KR    200445462 Y1    7/2009
RU      2088221 C1    8/1997
WO   2010/093173 A3   8/2010

* cited by examiner

SANITIZING MACHINE

The present invention relates to a machine capable of sanitizing and/or disinfecting storage containers, such as bags, duffel-bags, suitcases and/or other containers transiting in the holds of aircraft, ships and luggage rooms, as well as containers which can be transported in railway stations, in halls at fairs and/or in the rooms of hospitals, clinics, barracks, nursing homes, schools, nursery schools, etc.; the invention also relates to the related sanitizing process.

It is known that in public or private areas frequented by many people the concentration of harmful pathogens, such as bacteria, is extremely high and that said pathogens can easily contaminate objects and/or other common use tools.

The risk of contamination increases the chance of infection and compromises the health of the people in the rooms of houses where said objects and/or tools are placed.

The present invention intends to overcome the above mentioned drawbacks of the prior art.

In particular, the main object of the invention is to provide a sanitizing machine, which can be installed in public or private areas and which can be used, free or paid, for preventing the contamination of objects, such as bags, suitcases, bags, etc., in order to protect people from contamination and in order to preserve the hygiene in the rooms of houses where said objects are usually placed after use.

Another object of the present invention is to provide a sanitizing machine, which is simple and economical and which provides an easy and quick maintenance, as well as an effective and reliable operation.

A further object of the present invention is to indicate a sanitizing method which can be implemented by the above mentioned machine.

These and other objects are achieved by a sanitizing machine according to the appended claim 1, and by a related method according to the appended claim 4; other detailed technical characteristics of the machine are claimed in the other appended claims.

Advantageously, the present invention relates to a sanitizing machine which is configured to sanitize and to disinfect luggage, such as bags, duffel-bags, suitcases and/or other common use objects.

The disinfection is simply and quickly carried out and allows to remove pathogens which accumulate on said objects in airports, cruise-ships cargos, aircrafts cargos, railway stations, schools, hospitals, clinics, nursing homes, halls at fairs, etc.

Said disinfection is useful for the user as it is possible to prevent contamination of the objects by using, free or paid, said machine and, therefore, to preserve the hygiene in the domestic environment where said objects are stowed away after their use.

The above mentioned objects and advantages, as well as others that will be better described in the following, will be more clear from the following description, which relates to a preferred embodiment of the sanitizing machine, which is the object of the present invention, and also referring to the enclosed drawings, in which.

Firstly, please note that, even if the following description specifically refers to suitcases or luggage that can be sanitized within the machine according to the invention and even if the description specifically refers to a machine that can be advantageously installed in airports, both in the conveyor chain of the luggage, at the check-in counters, and in other airport locations, the above invention is extended to any machine capable of sanitizing and/or disinfecting storage containers, such as bags, hand-bags, suitcases and other luggage transiting through the holds of aircraft and ships and through the luggage storage, as well as transiting in railway stations, in the halls of fairs and/or in the rooms of hospitals, clinics, barracks, nursing homes, schools, nursery schools, etc.

With reference to the above mentioned figures, the sanitizing machine according to the invention is structurally constituted by a supporting frame, made of stainless steel, and with buffering perimeter panels, made of sheet steel or plastic, and is divided into two chambers or compartments, which are provided on the front side of the machine and which are respectively indicated with A and B in the enclosed figures.

Figure 1:
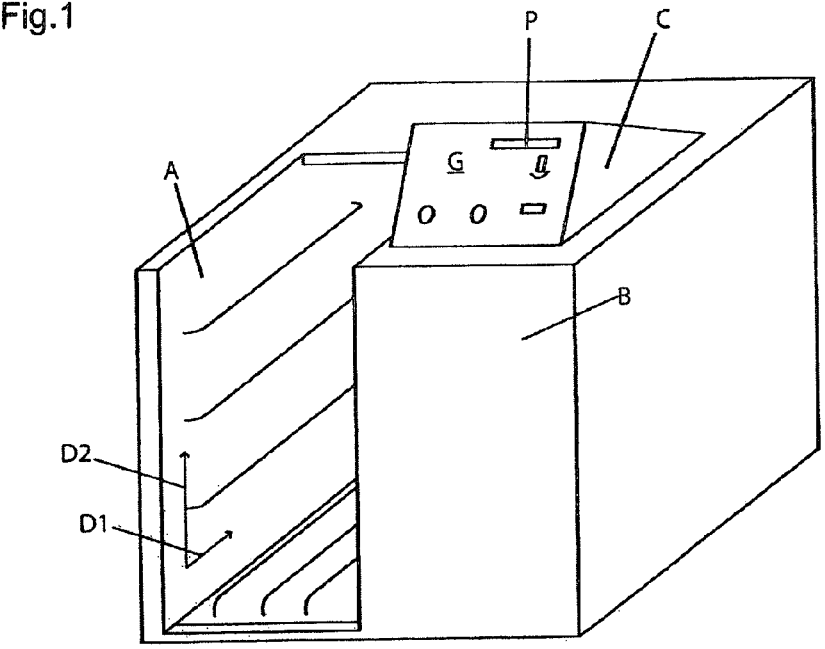
FIG. 1 is a perspective view of the sanitizing machine, according to the present invention, in an open position.

When the machine is at rest (or in standby), chamber A is open and is usable to insert the suitcase V to sanitize; the suitcase V can be easily introduced into the compartment A since the machine is open, at least partially, also in its upper part (as shown in the enclosed FIG. 1) and this allows the insertion and/or the withdrawal of the suitcase V both in a direction which is parallel to the ground (the direction indicated by the arrow D1 in the enclosed FIG. 1) and than in a direction which is orthogonal to the ground (the direction indicated by the arrow D2 in the enclosed FIG. 1).

Figure 2:
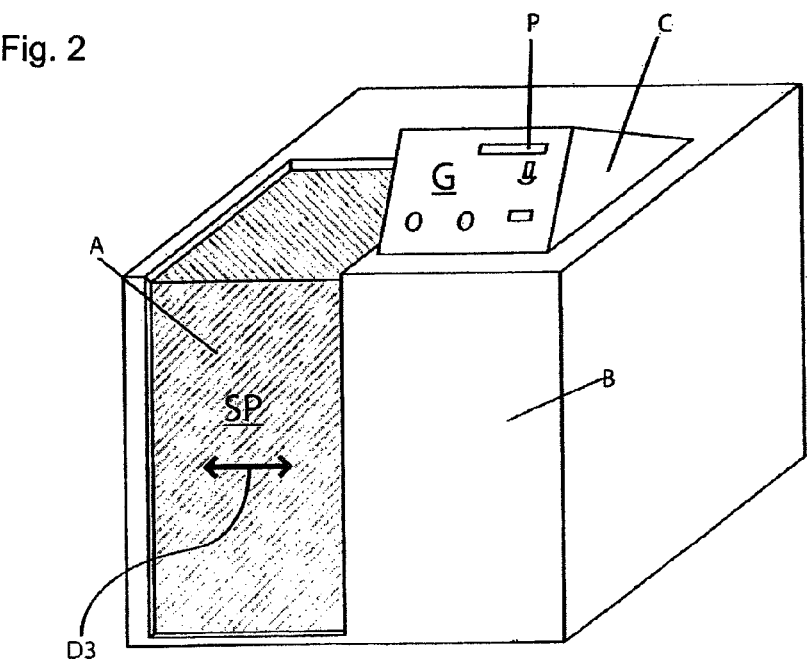
FIG. 2 is a perspective view of the sanitizing machine, according to the invention, in a closed and working position.

The compartment B of the machine houses a sliding door SP, which can be retractable and which moves along the direction of the arrows D3 of the enclosed FIG. 2, so as to automatically close and seal the compartment A during the working cycle of the machine.

The compartment B also houses the power equipments of the machine, such as an air compressor and an ozone generator, the electrical devices and a tank containing the disinfectant liquid.

A front portion C of the machine, which is provided above the compartment B, includes a coin acceptor G, with activation and/or command buttons for controlling and choosing the sanitizing cycle, and a monitor or display P signaling the waiting time and other relevant instructions for use of the machine.

The sanitizing machine, which operates according to well-defined and user-selectable working cycles, is on only after the user has placed the suitcase V inside the compartment A, has inserted coins and/or tokens (or other type of electronic money) inside the coin acceptor G, has chosen the desired sanitizing cycle (through suitable buttons placed on the coin acceptor G) and has activated a starting button of the machine (which usually consists of a starting double-button).

The activation of a power button of the machine causes the automatic closing of the sliding door SP, which is always closed during the sanitizing cycle, as well as the automatic reopening of the door SP at the end of the cycle, which will again allow the withdrawal of the suitcase V at the end of the working cycle.

Figure 3:
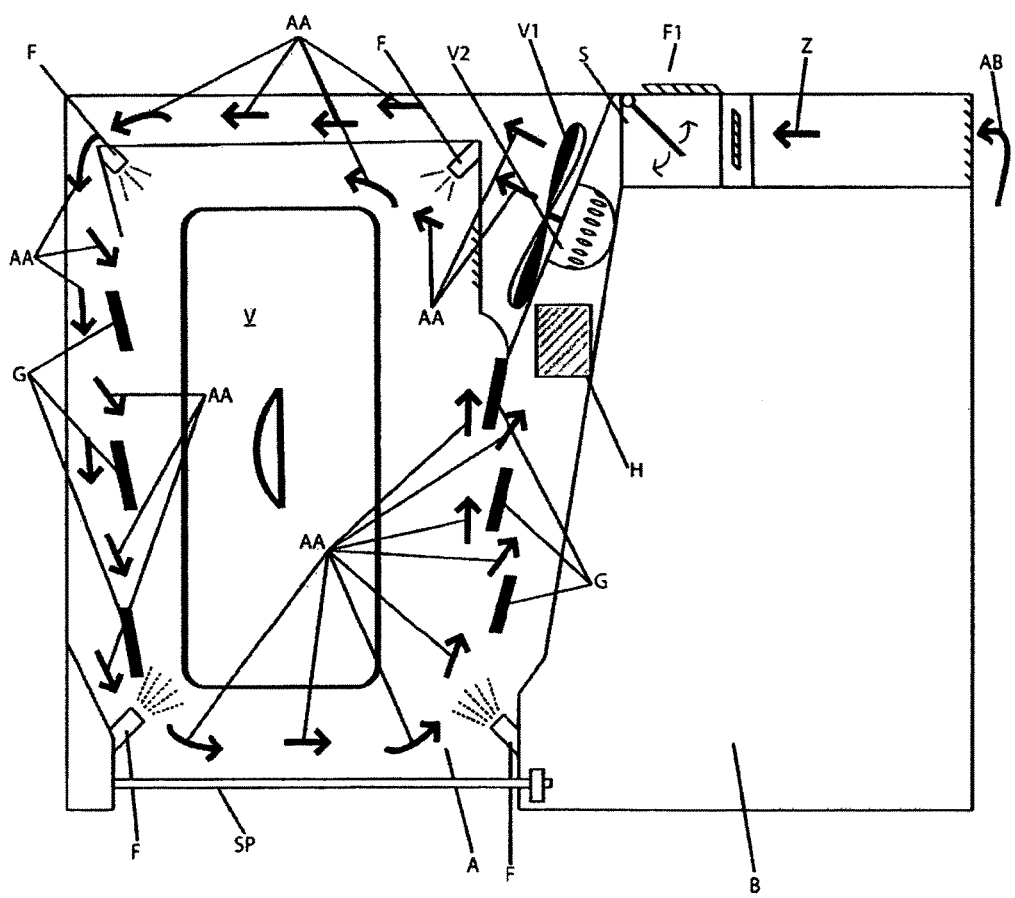
FIG. 3 is a section view of the sanitizing machine, according to the present invention, in which the sanitizing flows are schematically shown.

With particular reference to the enclosed FIG. 3, sanitization cycles that can be performed by the machine according to the invention include a ozone cycle, a sanitizing liquid cycle and a combined cycle (ozone+liquid).

The ozone cycle is performed by blowing ozone (arrow Z in the enclosed FIG. 3) inside the compartment A of the machine where it is placed the suitcase V to sanitize; ozone is blown through a damper access S placed at the end of a lower duct equipped with an active carbon filter F1 and, in particular, ozone Z is blown mixed with air (arrow AB in the enclosed FIG. 3) with prefixed concentrations and by means of a suitable generator and a relative fan V1, which ensures a suitable and homogeneous involvement of the entire surface of the suitcase V within a predetermined time (typically equal to approximately 50 seconds).

Alternatively, it is possible to provide a working cycle with sanitizing liquid, according to which a forced ventilation of air AA enclosed in the compartment A where the suitcase V is placed is firstly performed, by means of the fan V1 and for a predetermined time (typically about 20 seconds), in order to neutralize any static charge, thus favoring the homogeneous adhesion of the sanitizing liquid to the surface of the suitcase V.

The sanitizing liquid is taken from a suitable tank according to prefixed doses, by means of a pump, and is atomized, by means of spray nozzles F, which operate according to the Venturi principle and which are provided as a loop both in a lower portion and in an upper portion near the suitcase V.

The sanitizing liquid is sprayed after the forced ventilation phase and for a predetermined time of about 2-3 seconds; afterwards, a quick restart of a phase of forced ventilation is provided by means of the fan V1.

A plurality of baffles G, suitably shaped and arranged around the suitcase V, are also provided for carrying out a complete mixing between the sanitizing liquid which is sprayed and the air AA which is already forced to circulate inside the compartment A, without any unwanted turbulence and so as to obtain a complete adhesion of the sanitizing liquid to the entire surface of the suitcase V.

The forced ventilation made by the V1 and/or a further blowing of hot air which is performed for example through a drying fan V2 for another prefixed time (typically about 30 seconds) allow to completely remove the sanitizing liquid by drying it and by condensing it; the sanitizing liquid is therefore retained, together with other impurities and residual particles, inside the upper "HEPA" or active carbons filter H (which may be periodically replaced).

According to other embodiments of the invention, it is possible to set a combined cycle according to which an ozone blowing phase and a sanitizing liquid spraying phase are performed; in particular, an ozone blowing, as described above, is performed for a predetermined time (typically equal to about 40 seconds) and afterwards a spraying (atomization) phase of the sanitizing liquid together with a subsequent ventilation phase of the compartment A are performed, in order to obtain a complete drying of the suitcase V.

From the above description, therefore, it is clear that the sanitizing machine and the sanitizing method thereof, which are the object of the present invention, achieve the objects and the advantages which have been previously mentioned.

Finally, please consider that the present description has been made with the only purpose to illustrate and describe preferred embodiments of the invention and therefore it cannot limit in any way the scope of protection of said invention according to the appended claims.

The invention claimed is:

1. Sanitizing machine comprising a supporting structure which includes at least two compartments or chambers (A, B), said compartments or chambers (A,B) being arranged side by side and characterized in that at least one first compartment (B) of the sanitizing machine houses power equipment and at least one tank containing a sanitizing liquid, while at least one second compartment (A) of the sanitizing machine, when said sanitizing machine is in stand-by, is open for placing at least one container or object (V) to be sanitized, said sanitizing machine having spraying nozzles (F) which are placed inside said at least one second compartment (A) as a loop around said container or object (V) said sanitizing machine also having shaped baffles (G) arranged around said container or object (V) to be sanitized, in order to obtain a complete mixing between sprayed sanitizing liquid and forced air (AA) which is circulated within said at least one second compartment (A), to obtain a complete adhesion of the sprayed sanitizing liquid to the entire surface of said container or object (V) to be sanitized, and having a fan (V1) for air-forced ventilation of said at least one second compartment (A) when said container or object (V) is placed inside said at least one second compartment (A); said at least one second compartment (A) of the sanitizing machine having an opening which is tightly and automatically closable and reopenable, by means of at least one closing door (SP), when the sanitizing machine is on, said at least one closing door (SP) being a sliding retractable door and said opening being constructed to allow said container or object (V) to be inserted or withdrawn from said at least one second compartment (A) of the sanitizing machine both according to a direction (D1) which is parallel to the ground on which the sanitizing machine rests and according to a direction (D2) which is orthogonal to said ground.

2. Sanitizing machine as claimed in claim 1, characterized in that a prefixed portion (C) of the sanitizing machine comprising a coin acceptor (G) is provided above said at least one first compartment (B), said prefixed portion (C) housing activation and/or control buttons for choosing a working cycle of the sanitizing machine and a display device (P) for displaying waiting times and instructions for use of the sanitizing machine.

3. Sanitizing machine as claimed in claim 1, characterized in that a prefixed portion (C) of the sanitizing machine comprising a coin acceptor (G) is provided above said at least one first compartment (B), said prefixed portion (C) housing activation and/or control buttons for choosing a working cycle of the sanitizing machine and a display device (P) for displaying waiting times and instructions for use of the sanitizing machine.

4. A method for sanitizing containers or objects (V) by means of a sanitizing machine according to claim 1, characterized by comprising at least the following phases:
inserting at least one container or object (V) within said at least one second compartment (A) of the sanitizing machine;
choosing a working cycle of the sanitizing machine among a working ozone cycle, a working sanitizing liquid cycle and a working combined cycle;
activating a push-button of the sanitizing machine, thus causing an automatic closing of said door (SP), which is closed during the working cycle of the machine;
withdrawing said container or object (V) from said at least one second compartment (A) of the sanitizing machine.

5. A method for sanitizing containers or objects (V) as claimed in claim 4, characterized in that said ozone cycle provides for at least the following phases:
blowing, for a prefixed time, a mixture of ozone (Z) and air (AB) within said at least one second compartment (A) where said container or object (V) to sanitize is placed, through a damper access (S) which is positioned within a duct with at least one first active carbon filter (F1), and by means of fan (V1).

6. A method for sanitizing containers or objects (V) as claimed in claim 5, characterized in that said sanitizing liquid cycle includes at least the following phases:

air-forced ventilating (AA), for a first prefixed time, said at least one second compartment (A) when said container or object (V) to sanitize is placed inside said at least one second compartment (A);

stopping said air-forced ventilating phase and spraying said sanitizing liquid for a second prefixed time, which is less than said first prefixed time, by means of spraying nozzles (F) which are placed as a loop around said container or object (V) to sanitize;

quick restarting of said air-forced ventilating (AA) phase.

7. A method for sanitizing containers or objects (V) as claimed in claim 6, characterized in that, after said phase of restarting of air forced ventilation, hot air is again blown for a prefixed time, in order to dry or condense or retain the liquid within at least one second active carbon filter (H).

8. A method for sanitizing containers or objects (V) as claimed in claim 4, characterized in that said sanitizing combined cycle includes combined phases of blowing ozone and spraying sanitizing liquid for relative prefixed times, with a final phase according to which air-forced ventilation is provided within said at least one second compartment (A) where said container or object (V) to sanitize is placed, so as to obtain a complete drying of said container or object (V).

\* \* \* \* \*